(12) United States Patent
Tsern et al.

(10) Patent No.: US 11,351,335 B2
(45) Date of Patent: Jun. 7, 2022

(54) SLEEP PHASE DEPENDENT PRESSURE CONTROL AND LEARNING METHODS TO OPTIMIZE SLEEP QUALITY

(71) Applicants: Ely Tsern, Los Altos, CA (US); Jonathan Farringdon, Pittsburgh, PA (US); John Tompane, Los Altos, CA (US); Adam Hamel, Bradenton, FL (US); Mark Handel, Pittsburgh, PA (US)

(72) Inventors: Ely Tsern, Los Altos, CA (US); Jonathan Farringdon, Pittsburgh, PA (US); John Tompane, Los Altos, CA (US); Adam Hamel, Bradenton, FL (US); Mark Handel, Pittsburgh, PA (US)

(73) Assignee: Bryte, Inc., Los Altos, CA (US)

( * ) Notice: Subject to any disclaimer, the term of this patent is extended or adjusted under 35 U.S.C. 154(b) by 195 days.

(21) Appl. No.: 16/401,064

(22) Filed: May 1, 2019

(65) Prior Publication Data

US 2019/0336720 A1    Nov. 7, 2019

Related U.S. Application Data

(60) Provisional application No. 62/665,283, filed on May 1, 2018.

(51) Int. Cl.
*A61M 21/02* (2006.01)
*A61B 5/00* (2006.01)
(Continued)

(52) U.S. Cl.
CPC ............... *A61M 21/02* (2013.01); *A61B 5/11* (2013.01); *A61B 5/4815* (2013.01);
(Continued)

(58) Field of Classification Search
CPC ... A47C 21/044; A47C 23/047; A47C 23/002; A47C 21/048; A47C 21/003;
(Continued)

(56) References Cited

U.S. PATENT DOCUMENTS 7,524,279 B2    4/2009    Auphan
7,967,739 B2    6/2011    Auphan
(Continued)

FOREIGN PATENT DOCUMENTS

KR    10-2016-0030737 A    3/2016
KR    10-2017-0065853 A    6/2017
(Continued)

OTHER PUBLICATIONS

International Search Report on related PCT Application No. PCT/US2019/030281 from International Searching Authority (KIPO) dated Aug. 7, 2019.
(Continued)

*Primary Examiner* — Christine H Matthews
*Assistant Examiner* — Joshua Daryl D Lannu
(74) *Attorney, Agent, or Firm* — Klein, O'Neill & Singh, LLP

(57) ABSTRACT

A bed includes components to control pressure of a sleep surface, for example based on sleep position and sleep stages of a user. In some embodiments target pressures for the sleep surface are iteratively adjusted over multiple sleep sessions so to achieve improvements in sleep states and/or sleep quality for the user.

8 Claims, 7 Drawing Sheets

(51) Int. Cl.
*A61B 5/11* (2006.01)
*A61M 21/00* (2006.01)

(52) U.S. Cl.
CPC .......... *A61B 5/6892* (2013.01); *A61B 5/4812* (2013.01); *A61B 5/6891* (2013.01); *A61B 2562/0247* (2013.01); *A61M 2021/0066* (2013.01)

(58) Field of Classification Search
CPC ... A47C 31/008; A47C 31/123; A47C 27/083; A47C 27/061; A61M 2205/3584; A61M 2205/3344; A61M 2209/088; A61M 2230/40; A61M 2230/06; A61M 2205/3553; A61M 2230/50; A61M 2205/332; A61M 2230/62; A61M 2205/50; A61M 2210/10; A61M 2021/0066; A61M 2205/3592; A61M 2205/3368; A61M 2205/3569; A61M 2021/0027; A61M 21/02; A61M 2021/0083; A61M 2021/0022; A61M 2230/005; A61M 2205/84; A61M 2205/505; A61M 2205/3606; A61B 5/6891; A61B 5/11; A61B 5/6805; A61B 2562/0247; A61B 5/4815; A61B 5/6892; A61B 5/4812; A61B 5/0816; A61B 5/024; A61B 5/1116; A61B 2560/0242; A61B 5/01
See application file for complete search history.

(56) References Cited

U.S. PATENT DOCUMENTS

| | | |
|---|---|---|
| 8,161,826 B1 | 4/2012 | Taylor |
| 8,533,879 B1 | 9/2013 | Taylor |
| 8,661,915 B2 | 3/2014 | Taylor |
| 8,690,751 B2 | 4/2014 | Auphan |
| 8,800,386 B2 | 8/2014 | Taylor |
| 9,642,470 B2 | 5/2017 | Taylor |
| 10,744,390 B1 | 8/2020 | Kahn et al. |
| 10,945,659 B1 | 3/2021 | Kahn et al. |
| 2013/0283530 A1 | 10/2013 | Main et al. |
| 2015/0087894 A1* | 3/2015 | Rink ................ A61M 21/02 600/28 |
| 2015/0351982 A1* | 12/2015 | Krenik ............. A61G 7/018 5/616 |
| 2016/0015184 A1* | 1/2016 | Nunn ................ A47C 27/082 700/282 |

FOREIGN PATENT DOCUMENTS

| | | | |
|---|---|---|---|
| WO | WO 2005-107674 A2 | 11/2005 | |
| WO | WO-2005107674 A2 * | 11/2005 | ........... A61B 5/1118 |
| WO | WO 2018-023135 A1 | 2/2018 | |

OTHER PUBLICATIONS

Written Opinion on related PCT Application No. PCT/US2019/030281 from International Searching Authority (KIPO) dated Aug. 7, 2019.

Extended European Search Report on related European Patent Application No. 19797019.7 from the European Patent Office (EPO) dated May 20, 2021.

Office Action of related Chinese Application No. 201980036947.9 from China National Intellectual Property Administration dated Dec. 17, 2021.

* cited by examiner

Sleep Stage

|  | | N1 | N2 | N3 | N4 | REM |
|---|---|---|---|---|---|---|
| P O S I T I O N | side | $S_1$ | $S_2$ | $S_3$ | $S_4$ | $S_5$ |
| | side-fetal | $Sf_1$ | $Sf_2$ | $Sf_3$ | $Sf_4$ | $Sf_5$ |
| | back | $b_1$ | $b_2$ | $b_3$ | $b_4$ | $b_5$ |
| | front | $f_1$ | $f_2$ | $f_3$ | $f_4$ | $f_5$ |

FIG. 6

SLEEP PHASE DEPENDENT PRESSURE CONTROL AND LEARNING METHODS TO OPTIMIZE SLEEP QUALITY

CROSS-REFERENCE TO RELATED APPLICATION

This application claims the benefit of U.S. Provisional Patent Application No. 62/665,283, filed May 1, 2018, the subject matter of which is incorporated herein by reference in its entirety.

BACKGROUND OF THE INVENTION

The present invention relates generally to sleep environments, and more particularly to firmness control of a sleep surface, including firmness control of multiple zones of a sleep surface on a zone-by-zone basis.

Sleep is a universal need for people. Sleep provides many physiological benefits, and a sound night's sleep is often desired by many. Unfortunately, some may not obtain good quality sleep, even when sufficient time and preparation for sleep is available.

BRIEF SUMMARY OF THE INVENTION

Some embodiments in accordance with aspects of the invention provide for control of pressure on a sleep surface based on a sleep position and/or sleep stage, or lack thereof, of a sleeper. In some embodiments the sleep surface includes multiple zones, with pressure separately controllable for each of the multiple zones. In some embodiments a bed includes pressure devices used in adjusting firmness of a sleep surface of a bed; pressure sensors for sensing an indication of pressure of the sleep surface; and a controller configured to command the pressure devices to target pressures, indicated by target pressure profiles, based on a sleep position and/or sleep stage, or lack thereof, of a sleeper. In some embodiments the sleep surface includes multiple zones, with pressure separately controllable for each of the multiple zones. In some such embodiments the pressure devices include pressure devices used in adjusting firmness of each of different zones of the multiple zones of the sleep surface. In some such embodiments the pressure sensors include pressure sensors for sensing an indication of pressure for each of the different zones of the multiple zones. In some embodiments the controller is further configured to command the pressure devices to test pressures instead of the target pressures of a particular target pressure profile; determine if a sleep criteria for the sleeper indicates improved sleep using the test pressures instead of the target pressures of the particular target pressure profile; and, in response to determining that the sleep criteria for the sleeper indicated improved sleep, replace the pressures of the particular target pressure profile with the test pressures.

Some embodiments provide a bed including a sleep surface having controllable firmness, comprising: pressure devices used in adjusting firmness of the sleep surface; pressure sensors configured to sense indications of pressure of the sleep surface; and a controller configured to command the pressure devices to target pressures, as indicated by at least one target pressure profile specifying the target pressures; with the controller further configured to, from time-to-time: command the pressure devices to test pressures instead of at least some of the target pressures specified by the at least one target pressure profile; determine if a sleep metric for a sleeper on the sleep surface indicates improved sleep performance using the test pressures instead of the target pressures specified by the at least one target pressure profile; and, in response to determining that the sleep metric for the sleeper indicates improved sleep performance, replace the at least some of the target pressures specified by the at least one target pressure profile with the test pressures.

In some embodiments the sleep surface includes multiple zones, with different pressure devices for each of the multiple zones. In some embodiments the controller is configured to command different target pressures for at least some of the different pressure devices of different ones of the multiple zones. In some embodiments the pressure sensors include pressure sensors for sensing an indication of pressure for each of the different ones of the multiple zones. In some embodiments the at least one target pressure profile is associated with the sleeper. In some embodiments the at least some of the target pressures are target pressures of a pre-sleep profile associated with the sleeper. In some embodiments the sleep metric for the sleeper indicates improved sleep performance if the sleeper falls asleep faster. In some embodiments the sleep metric for the sleeper comprises an amount of slow wave sleep. In some embodiments the sleep metric for the sleeper comprises an amount of sleep in a predetermined sleep stage. In some embodiments the sleep metric is an amount of sleep in a sleep stage deeper than a predetermined sleep stage. In some embodiments the sleep metric for the sleeper comprises a total sleep time. In some embodiments the total sleep time is a period of time from a time the sleeper fell asleep to a time the sleeper awoke, minus any time periods in which the sleeper is considered awake during the period of time. In some embodiments the time periods in which the sleeper is considered awake includes brief periods in which the sleeper had excursions from deeper sleep stages to lighter sleep stages. Some embodiments further comprise biometric sensors configured to provide biometric information regarding the sleeper. In some embodiments the controller is further configured to determine sleep stages of the sleeper based on the biometric information regarding the sleeper. In some embodiments the at least one target pressure profile specifies different target pressures at different times. In some embodiments the at least one target pressure profile comprises a plurality of target pressure profiles. In some embodiments each of the plurality of target pressure profiles are associated with different sleep stages. In some embodiments the controller is further configured to command the pressure devices to different target pressures at different rates based on a sleep stage of the sleeper. In some embodiments rates for lighter sleep stages are slower than rates for deeper sleep stages. In some embodiments the plurality of target pressure profiles include different target pressure profiles for each of a plurality of sleep positions and a plurality of sleep stages. In some embodiments the controller is further configured to determine a sleep position of the sleeper based on information from the pressure sensors. In some embodiments the plurality of target pressure profiles include different target pressure profiles for each of a plurality of sleep stages. In some embodiments the controller is configured to utilize the test pressures over multiple nights, and to use a statistically calculated value for the sleep metric. In some embodiments the statistically calculated value is an average. In some embodiments the controller is configured to begin commanding the pressure devices to the target pressures, or the test pressures, in response to receiving an indication that the sleeper is on the sleep surface. In some embodiments the controller is configured to command the pressure devices to target pressures specified by a sleep target pressure profile in response to receiving an indication from biometric sensors that the sleeper is asleep. In some embodiments the pre-sleep profile specifies target pressures that vary over time. In some embodiments the pre-sleep profile specifies target pressures that vary over time in a repetitive pattern. In some embodiments the controller is further configured to command play of audio having content synchronized with variations in commanded target pressures. In some embodiments at least one sleep target pressure profile provides for target pressures that vary over time. In some embodiments the controller is further configured to monitor the biometric information, and modifies use of the at least one sleep target pressure profile based on the monitored biometric information. In some embodiments the modification of use of the at least one sleep target pressure profile is a cessation of use of the at least one sleep target pressure profile.

Some embodiments provide a method of conditioning a bed with a sleep surface having controllable firmness, comprising: commanding pressure devices to target pressures, specified by at least one target pressure profile, with the pressure devices being under the sleep surface of the bed; and from time-to-time: commanding the pressure devices to test pressures instead of the target pressures specified by the at least one target pressure profile; determining if a sleep metric for a sleeper on the sleep surface indicates improved sleep performance using the test pressures instead of the target pressures of the at least one target pressure profile; and in response to determining that the sleep metric for the sleeper indicates improved sleep, replacing the target pressures of the at least one target pressure profile with the test pressures.

In some embodiments the pressure devices include different pressure devices for different zones of a plurality of zones of the sleep surface. In some embodiments at least some of the target pressures are different pressures for the different pressure devices for the different zones. In some embodiments the pressure sensors include pressure sensors for sensing an indication of pressure for each of the different ones of the multiple zones. In some embodiments the at least one target pressure profile is associated with the sleeper. In some embodiments the at least some of the target pressures are target pressures of a pre-sleep profile associated with the sleeper. In some embodiments the sleep metric for the sleeper indicates improved sleep if the sleeper falls asleep faster. In some embodiments the sleep metric for the sleeper comprises an amount of slow wave sleep. In some embodiments the sleep metric for the sleeper comprises an amount of sleep in a sleep stage deeper than a predetermined sleep stage. In some embodiments the sleep metric for the sleeper comprises a total sleep time. In some embodiments the total sleep time is a period of time from a time the sleeper fell asleep to a time the sleeper awoke, minus any time periods in which the sleeper is considered awake during the period of time. In some embodiments the time periods in which the sleeper is considered awake includes brief periods in which the sleeper had excursions from deeper sleep stages to lighter sleep stages. In some embodiments the controller is further configured to determine sleep stages of the sleeper based on the biometric information from biometric sensors. In some embodiments the at least one target pressure profile specifies different target pressures at different times. In some embodiments the at least one target pressure profile comprises a plurality of target pressure profiles. In some embodiments each of the plurality of target pressure profiles are associated with different sleep stages. In some embodiments the pressure devices are commanded to different target pressures at different rates based on a sleep stage of the sleeper. In some embodiments rates for lighter sleep stages are slower than rates for deeper sleep stages. In some embodiments the plurality of target pressure profiles include different target pressure profiles for each of a plurality of sleep positions and a plurality of sleep stages. In some embodiments the plurality of target pressure profiles include different target pressure profiles for each of a plurality of sleep stages. In some embodiments the test pressures are utilized over a plurality of sleep sessions, and the sleep metric is a statistically calculated value based on information over the plurality of sleep sessions. In some embodiments the pressure devices are commanded to the target pressures in response to receiving an indication that the sleeper is on the sleep surface. In some embodiments the pre-sleep profile specifies target pressures that vary over time in a repetitive manner. Some embodiments further comprise commanding play of audio having content synchronized to variation of target pressures specified by the pre-sleep profile. Some embodiments further comprise modifying use of the at least one target pressure profile based on the biometric information.

Some embodiments provide a bed including a sleep surface having controllable firmness, comprising: pressure devices used in adjusting firmness of the sleep surface; and a controller configured to command the pressure devices to target pressures, as indicated by at least one target pressure profile specifying target pressures, at a rate of change based on a sleep stage of a sleeper on the sleep surface.

Some embodiments further comprise biometric sensors configured to provide biometric information regarding the sleeper, and the controller is further configured to determine the sleep stage of the sleeper based on the biometric information. In some embodiments the at least one target pressure profile comprises a plurality of target pressure profiles, and the controller is further configured to determine the sleep stage of the sleeper based on the target pressure profile then being used by the controller. In some embodiments the rate of change for lighter sleep stages is less than the rate of change for deeper sleep stages.

Some embodiments provide a method of conditioning a bed with a sleep surface having controllable firmness, comprising: determining target pressures for pressure devices under the sleep surface of the bed; changing pressures for at least some of the pressure devices to the target pressures, at a rate of change in pressure dependent on a sleep stage of a sleeper on the sleep surface. In some embodiments the rate of change for lighter sleep stages is less than the rate of change for deeper sleep stages.

These and other aspects of the invention are more fully comprehended upon review of this disclosure.

BRIEF DESCRIPTION OF THE FIGURES

FIG. 6 is a table of pressure settings for use in controlling firmness of a sleep surface based on sleeper position and sleep stage, in accordance with aspects of the invention.

DETAILED DESCRIPTION

Figure 1:
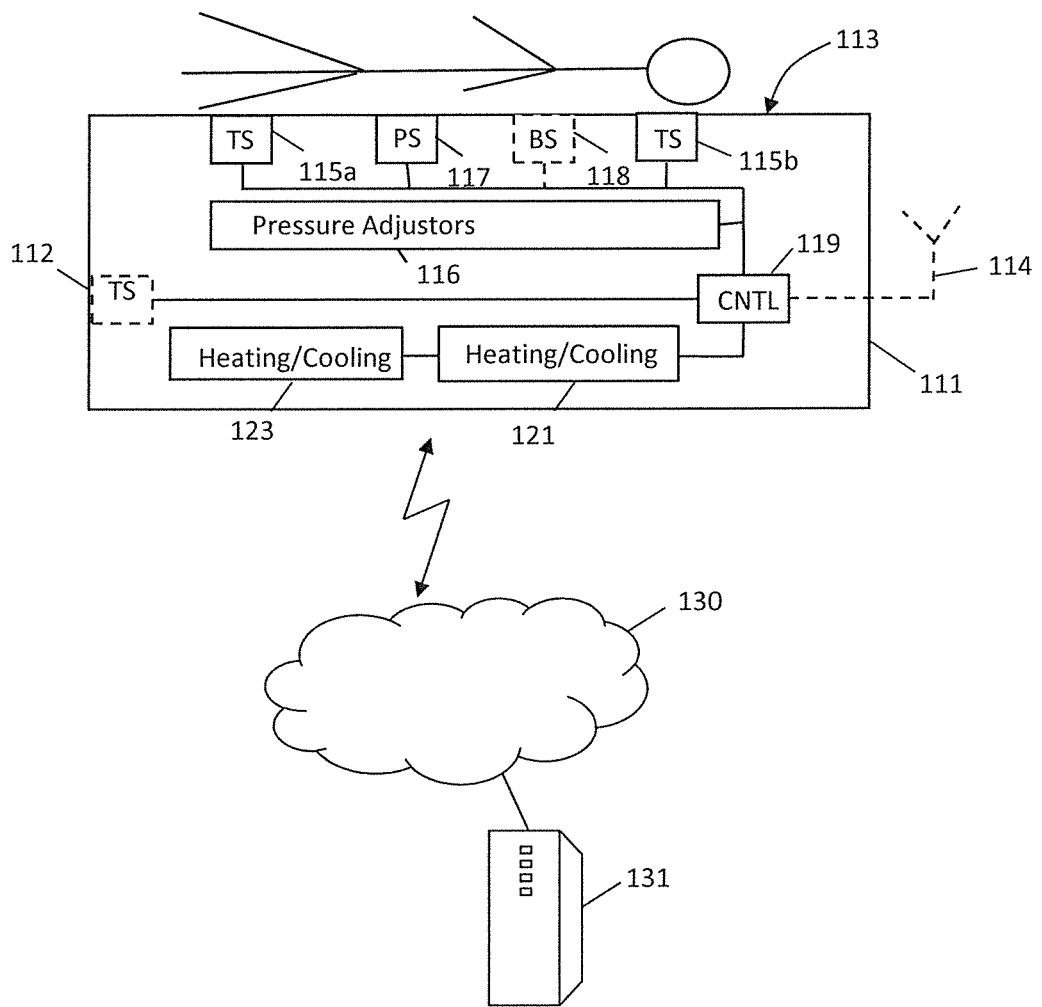
FIG. 1 is a semi-block diagram of a bed in accordance with aspects of the invention.

FIG. 1 is a semi-block diagram of a bed 111 in accordance with aspects of the invention. The bed of FIG. 1 includes a sleep surface 113 as an upper surface. In various embodiments, the sleep surface may be a top surface of a mattress, and in some embodiments the mattress, which itself may be comprised of multiple parts (separable or inseparable) may sit on top of a foundation, with the mattress and foundation considered the bed. In various embodiments, however, the bed may include other parts, and in some embodiments the various parts may be combined into one or more separable or non-separable items. The bed of FIG. 1 may be generally rectangular parallelepiped in form, although other forms may instead be used, and in various embodiments may house a variety of components and materials and be comprised of multiple separable components and/or layers. Generally a user, or multiple users depending on the bed, sleeps on the sleep surface.

The bed of FIG. 1 includes components for conditioning a sleep environment. For the example bed of FIG. 1, the components include a heating/cooling component 121 (and optional heating/cooling component 123) and a pressure adjustment component 116, which in some embodiments may include multiple sub-components, and which in some embodiments may instead be multiple pressure adjustment components, which may be more commonly simply termed as pressure devices. The heating/cooling component allows for adjustment of temperature of the sleep surface of the bed. The pressure adjustment component allows for adjustment of firmness of different zones on the sleep surface.

The components for conditioning the sleep environment are generally commanded to do so by a controller 119. In generating commands, the controller may do so using information from sensors, for example temperature sensors 115*a, b*, pressure sensors 117, and, in some embodiments, biometric sensors 118. The controller also may make use of additional information, for example time-of-day information (for example maintained by the controller), information provided by users by way of user devices, and historical usage and/or sensor information maintained by the controller. As illustrated in FIG. 1, the controller is housed within the bed. In various embodiments the controller can be housed in either the mattress, base or be located externally outside of the bed. In some embodiments the controller comprises one or more processors. In some embodiments the controller is comprised of more than one processor, and the controller may be partitioned and housed in at least two separate physical enclosures, each with at least one processor. In some embodiments the controller is comprised of more than one processor, and the controller may be partitioned and housed in at least two separate physical enclosures, each with at least one processor. In some embodiments the controller is coupled to a network by way of wired or wireless communication circuitry, which may include for example antenna 114. In such embodiments the controller may be coupled (for example by a network 130 which may include the Internet) to a remote server 131, which in some embodiments may perform various of the functions ascribed to the controller herein. In some embodiments the controller may also command play of audio, either by way of commands to an external audio device, provision of wireless audio signals to speakers external to the bed, or provision of audio signals to speakers (not shown) of the bed. The speakers of the bed may be (not shown) within or inset in a frame of the bed or of a portion of the bed.

The temperature sensors may be positioned in or adjacent the sleep surface, and provide an indication of a temperature of the sleep surface. In some embodiments, the temperature sensors are worn by the sleeper, provide an indication of a temperature of the sleeper's body or portion of body where the sensor is worn, and can be wired or wirelessly connected to the controller.

The pressure sensors may be located under the sleep surface, and provide an indication of pressure on the sleep surface. Alternatively, the pressure sensors may be located in the controller and connected via air tubes to air chambers, for example in the form of bladders, underneath the sleep surface to measure the pressure in the air chambers. The air chambers can be same or different sizes, and they can form independent zones individually or in groups. The biometric sensors may be located in or under the sleep surface, and may provide an indication of heart rate, breathing information, or other biometric information regarding the user on the sleep surface. In some embodiments the biometric sensors may be in an article worn by the user, for example a shirt, with the biometric sensors wirelessly communicating with the controller. In some embodiments the biometric sensors are as discussed or part of an item as discussed in J. Kelly et al., Recent Developments in Home Sleep-Monitoring Devices, ISRN Neurology, vol. 2012, article ID 768794, the disclosure of which is incorporated herein for all purposes. In some embodiments the controller uses the information from the biometric sensors to determine a sleep stage of the user. In some embodiments the sleep stage of the user may be considered to four stages of non-REM sleep—stages N1, N2, N3, N4, with stages N3 and N4 considered deep non-REM sleep or "slow-wave" sleep, —and one stage of REM sleep. In such embodiments, a user may be considered to typically undergo four full sleep cycles in a single night's sleep, with the first two sleep cycles being non-REM dominant and the last two sleep cycles being REM dominant. The first two sleep cycles typically include stage N1, N2, N3, N4 and REM, and the last two sleep cycles typically only include stages N1, N2, and REM. The sleep stage of the user may be determined using information from the biometric sensors, for example in manner utilizing or mimicking polysomnography techniques. In some embodiments the controller determines the sleep stage of the user by using one or more of its processors to compute the sleep stage based on information from the biometric sensors. In some embodiments, the controller communicates with a remote compute server over its communication interface, and the remote compute server computes the sleep stage based on biometric sensor information sent over the communication interface and may send sleep stage information back to the controller.

In some embodiments the pressure adjustment component comprises an array of controllable bladders or coils under the sleep surface of the bed. In some embodiments each of the controllable bladders or coils is individually adjustable, so as to provide a different level of firmness to the surface of the bed. In some embodiments the controllable bladders or coils are adjustable in groups, so as to provide a different level of firmness to the surface of the bed.

In some embodiments the controller commands the pressure adjustment component to provide a pre-sleep pressure profile for the sleep surface for use by the sleeper upon the sleeper first entering the bed. The pre-sleep pressure profile, in some embodiments, may be expected to result in a same pressure indication by all of the pressure sensors when the sleeper lies on the sleep surface prior to going asleep. In other embodiments the pre-sleep pressure profile may be expected to result in different pressure indications by the pressure sensor when the sleeper lies on the sleep surface prior to going to sleep. In some embodiments the controller may determine the pre-sleep pressure profile based on pressure information from the pressure sensors for prior sleeper usage of the bed. In some embodiments the controller stores pre-sleep pressure profiles for each of a plurality of sleepers. In some embodiments the controller utilizes different pre-sleep pressure profiles for different portions of the bed. For example, in some embodiments the controller utilizes a first pre-sleep pressure profile for a first side of the bed and a second pre-sleep pressure profile for a second side of the bed.

In some embodiments the controller may vary commands to the pressure adjustment component to provide different pressures than indicated by the pre-sleep pressure profile, for example to provide a different pre-sleep pressure profile. The controller may do so from time-to-time, generally on different days. The controller may then determine if the sleeper fell asleep faster with use of the different pre-sleep profile than with the previously used pre-sleep profile, and, if so, afterwards use the different pre-sleep profile as the pre-sleep profile for the user.

In some embodiments the controller may command the pressure adjustment component to vary surface pressures over time while the sleeper is in the bed prior to falling asleep. For example in some embodiments the controller may command the pressure adjustment component to vary pressures to different zones in various patterns and timings. The controller may also command play of audio, with content of the audio synchronized with the timings of variations in the commanded pressure.

In some embodiments the controller commands the pressure adjustment component to provide a sleep pressure profile for the sleep surface upon or after the sleeper falling asleep. As one would understand, with use of the sleep pressure profile upon or after the sleeper falling asleep, use of the pre-sleep profile would end. In some embodiments the sleep pressure profile may be one of several sleep pressure profiles for the sleeper. In some embodiments the several sleep pressure profiles include possibly different sleep pressure profiles for different sleep positions of the user and different sleep stages of the sleeper. In some embodiments the sleep pressure profiles may also specify audio associated with the sleep pressure profiles for use by the controller in commanding play of audio.

In some embodiments the controller commands the pressure adjustment component to change pressures at differing rates based on a sleep stage of the sleeper. For example, as the sleeper changes sleep position or sleep stage, the controller may command the pressure adjustment component to change pressures in accordance with a sleep profile for the new sleep position or sleep stage. In such embodiments, the controller may command the pressure adjustment component to change pressures at slower rates for lighter sleep stages, for example sleep stages N1 and N2, than for deeper sleep stages, for example N3 and N4, or slow wave sleep.

In some embodiments the controller may command the pressure adjustment component to change pressures using at least some pressures different than those which would otherwise have been specified for use by the several sleep profiles for the sleeper. The controller may do so from time-to-time, generally within a sleep session or on different days. The controller may then determine if a metric regarding sleep indicates that the sleeper indicates improved sleep performance for the sleeper with use of the different pressures than those which would otherwise have been specified for use. If so, the controller may change one or more of the several sleep profiles to include the different pressures. In some embodiments the metric may be an amount of slow wave sleep. In some embodiments the metric may be a total sleep time, with for example generally an increase in sleep time indicating improved sleep performance, as one would normally understand. In some embodiments a total sleep time may be considered a period from a time the sleeper fell asleep at night to a time the sleeper awoke in the morning, minus any time periods in which the sleeper was awake during the night after falling asleep. In some embodiments any time periods in which the sleeper had brief periods in which the sleeper had excursions from deeper sleep stages to lighter sleep stages may also be considered to be time the sleeper was awake. In some embodiments the brief period is less than six minutes. In some embodiments the brief period is less than two minutes. In some embodiments the brief period is less than one minute.

In some embodiments the controller may command the pressure adjustment component to change pressures to provide a wake-up pattern of varying pressures about a time the sleeper is expected to awaken. In some embodiments the varying pressures are provided in a wave-like form, for example increasing, for a short period of time, pressures starting at a head of a bed and proceeding to a foot of the bed, or vice-versa. In some embodiments the controller commands performance of the wake-up pattern based on a target wake-up time. In some embodiments the target wake-up time is set by the sleeper. In some embodiments the target wake-up time is based on a total sleep time or other sleep metric determined by the controller. In some embodiments the target wake-up time is based on a circadian rhythm of the sleeper determined by the controller. In some embodiments the controller additionally commands play of audio along with performance of the wake-up pattern. In some embodiments the audio includes content synchronized with the wake-up pattern.

In some embodiments the controller may command the pressure adjustment component to change pressures so as to increase firmness of the sleep surface after the sleeper awakens and prior to the sleeper leaving the bed. In some embodiments the controller determines if the sleeper has awoken based on information from biometric sensors. In some embodiments the controller may command the pressure adjustment component to increase a rate of variation of pressures after the target wake-up time if the sleeper has not awoken. For example, a frequency of a wave-like pattern (and/or its variation in amplitude) may be increased if the sleeper remains asleep after the target wake-up time, which in some embodiments is increasingly increased over time until the sleeper wakes up.

Figure 2:
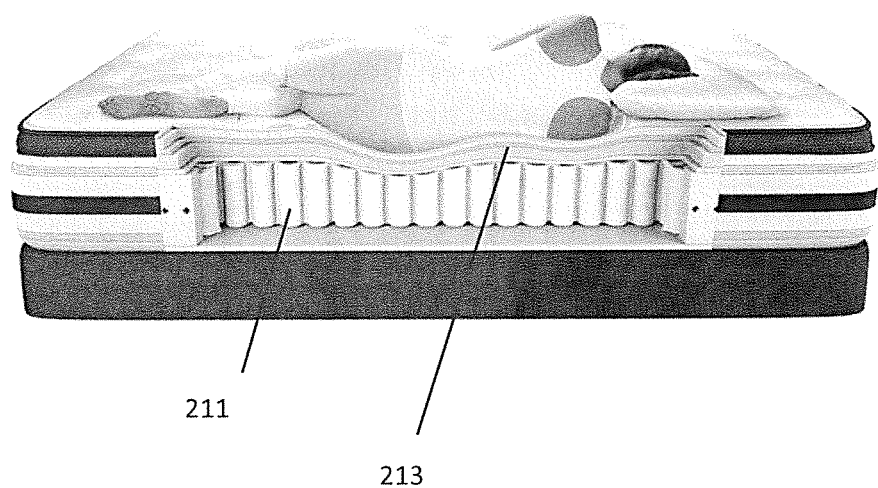
FIG. 2 is a semi-sectional side view of a bed in accordance with aspects of the invention, showing pressure adjustment cylinders holding bladders for adjusting firmness of the sleep surface.

FIG. 2 is a semi-sectional side view of a bed in accordance with aspects of the invention, showing pressure adjustment coil cylinders for adjusting firmness of the sleep surface. The bed of FIG. 3 includes a sensor layer 213 just underneath a sleep surface of the bed. Cylinders 211, which may have an open top through which may extend air (or fluid in some embodiments) bladders housed partially within the cylinders, are underneath the sensor layer, and provide adjustable support for a sleeper on the sleep surface.

Figure 3:
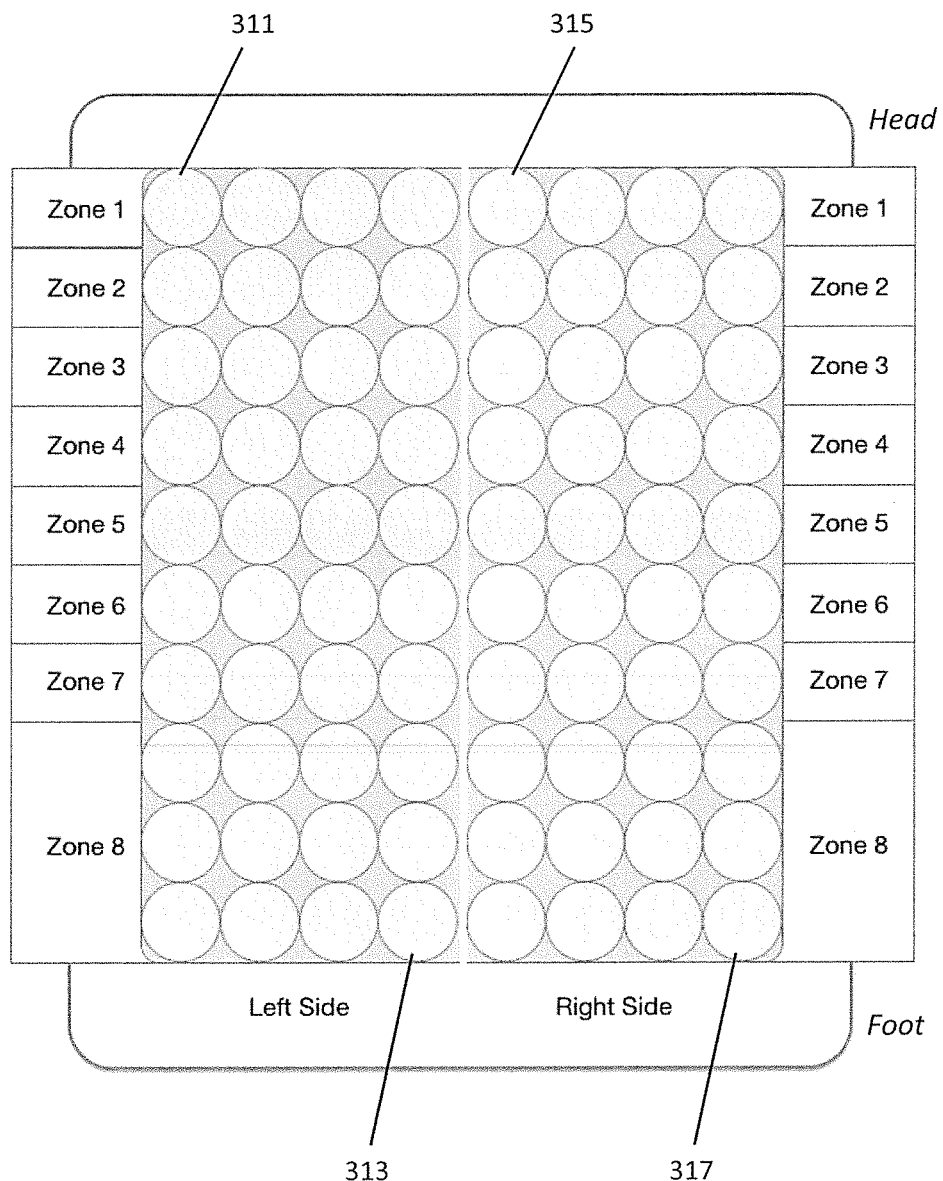
FIG. 3 is a semi-block diagram top view of pressure adjustment bladders locations of a bed with multiple zones in accordance with aspects of the invention.

FIG. 3 is a semi-block diagram top view of pressure adjustment bladders and indicating pressure sensor data locations of a bed in accordance with aspects of the invention. The bed includes a left side and a right side. Generally each side is sized to accommodate a sleeper. The bed also includes what may be termed a head of the bed, stretching across a first end of the left and right sides, with a foot of the bed at a second end, opposite the first end. Sleepers will generally position their heads toward the head of the bed, with their feet towards the foot of the bed.

The bed includes an array of pressure adjustment bladders. For the bed of FIG. 3, the array includes 80 bladders, arranged in a 10×8 array. In some embodiments each of the 80 bladders may be individually adjusted. For example, in some embodiments, pressure in each bladder or a group of bladders may be individually regulated, for example as commanded by the controller of FIG. 1. In some embodiments the array of pressure adjustment bladders may be considered as including two sub-arrays. For example, a first sub-array may include bladders 311-313 on a left side of the bed, and a second sub-array may include bladders 315-317 on a right side of the bed.

In some embodiments a pressure fabric or mat or the like may be used to provide pressure indications to a controller. In some embodiments a pressure sensor is associated with each of the bladders. In such embodiments, the controller may receive an indication of pressure on the sleep surface about the location of each of the bladders. In some such embodiments the pressure sensor is positioned in the bed between the bladder and a sleep surface of the bed. In other of some such embodiments, the pressure sensor is associated with an air valve of a bladder or group of bladders.

In some embodiments a pressure sensor is associated with a plurality of bladders. For example, in the embodiment of FIG. 3, a first pressure sensor may be associated with a portion of a row of bladders closest to the head and on the left side of the bed, a second pressure sensor may be associated with a portion of the row of closest to the head and on the right side of the bed, and so on for each row of bladders. Alternatively, some (or all) of the pressure sensors may be associated with bladders of multiple rows. For example, in FIG. 3, a single pressure sensor may be provided for 16 zones, with eight zones on the left side of the bed and eight zones on the right side of the bed, each zone, other than zones closest to the foot of the bed, being for a single row of bladders, with the zones closest to the foot of the bed being for three rows of bladders.

Figure 4:
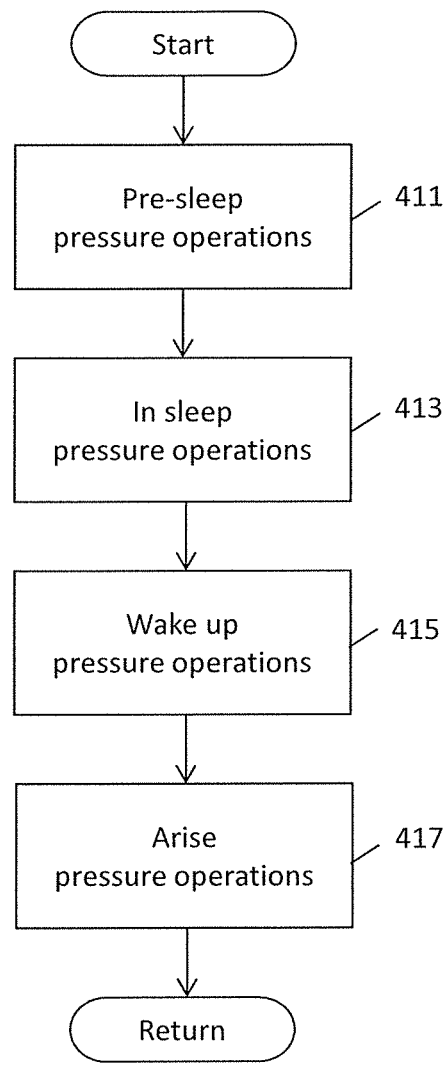
FIG. 4 is a flow diagram of a process for controlling firmness of a sleep surface of a bed in accordance with aspects of the invention.

FIG. 4 is a flow diagram of a process for controlling firmness of a sleep surface of a bed in accordance with aspects of the invention. In some embodiments the process is performed by a bed with a pressure adjustment component. In some embodiments the process is performed by a controller of a bed with a pressure adjustment component. In some embodiments the process is performed by a controller, which may be a processor, and in other embodiments, this computation is performed on a remote server coupled to the controller over a network. In some embodiments the processor receives information indicative of pressure on a sleep surface of a bed. In some embodiments the processor receives information from pressure sensors indicating pressure on at least a portion of the sleep surface, and in some embodiments the processor receives information from biometric sensors of the bed, or associated with a user of the bed.

In block 411 the process commands the pressure adjustment component to provide pressures of a pre-sleep pressure profile for at least a portion of the sleep surface. In some embodiments the pre-sleep pressure profile is a pre-sleep pressure profile for an identified sleeper. In some embodiments the pre-sleep pressure profile is for all of the sleep surface. In some embodiments the pre-sleep pressure profile is for a half of the bed which the identified sleeper is expected to use. In some embodiments the process commands the pressure adjustment component to provide pressures of a first pre-sleep pressure profile for a first half of the bed and pressures of a second pre-sleep pressure profile for a second half of the bed. In some embodiments the first pre-sleep pressure profile is for a first identified sleeper and the second pre-sleep pressure profile is for the second identified sleeper.

In some embodiments the process commands the pressure adjustment component to provide pressures of the pre-sleep pressure profile(s) at a predetermined time before sleeper(s) are expected to get into bed. In some embodiments the process commands the pressure adjustment component to provide pressures of the pre-sleep pressure profile(s) at a time after the sleeper(s) leave the bed and before sleeper(s) are expected to get into bed. In some embodiments the process commands the pressure adjustment component to provide pressures of the pre-sleep pressure profile(s) in response to receiving an indication that the sleepers, or at least one of them in some embodiments, have gotten into the bed.

In some embodiments the controller may vary commands to the pressure adjustment component to provide different pressures than indicated by the pre-sleep pressure profile, for example to provide a different pre-sleep pressure profile. The controller may do so from time-to-time, generally on different days, in order to determine if the sleeper falls asleep faster with the different pre-sleep pressure profile. In some embodiments the process may determine if the user has fallen asleep using information from biometric sensors. In some embodiments the process may utilize the different pre-sleep pressure profile multiple times across multiple nights, and use an average, or some other statistically calculated value, for determining whether the sleeper fell asleep faster with the different pre-sleep pressure profile than with the sleeper's then current pre-sleep pressure profile. In response to the controller determining that the sleeper fell asleep faster with use of the different pre-sleep pressure profile, the controller may set the different pre-sleep pressure profile as the pre-sleep pressure profile for the sleeper.

In some embodiments the pre-sleep profile may indicate pressures that vary over time. In some embodiments the pressures that vary over time do so in a repetitive pattern. In some embodiments the repetitive pattern is in the form of a wave or some other pattern.

In block 413 the process commands the pressure adjustment component to provide pressures of sleep pressure profiles for at least a portion of the sleep surface, with different ones of the sleep pressure profiles selected for use at any given time. As previously mentioned, the use of the sleep pressure profiles, in place of a pre-sleep pressure profile, may be done upon the sleeper falling asleep. The biometric sensors, in some embodiments, provide information as to when the sleeper falls asleep, in accordance with prior discussion regarding the biometric sensors. Thus, the sleep pressure profiles may be used in response to an indication from the biometric sensors that the sleeper has fallen asleep. In some embodiments the sleep pressure profiles are sleep pressure profiles for an identified sleeper. In some embodiments the sleep pressure profiles are for all of the sleep surface. In some embodiments the sleep pressure profiles are for a half of the bed which the identified sleeper is expected to use. In some embodiments the process commands the pressure adjustment component to provide pressures from a first set of sleep pressure profiles for a first half of the bed and pressures of a second set of sleep pressure profiles for a second half of the bed. In some embodiments the first set of sleep pressure profiles is for a first identified sleeper and the second set of sleep pressure profiles is for the second identified sleeper.

In some embodiments the sleep pressure profiles, for each sleeper, include a sleep pressure profile for each of several sleep positions. In some embodiments the sleep pressure profiles include a sleep pressure profile for each of several sleep stages. In some embodiments the sleep pressure profiles include sleep pressure profiles for each of several sleep positions and each of several sleep stages. In some embodiments some of the sleep pressure profiles may be the same for some of the sleep positions and/or sleep stages.

In some embodiments the process commands the pressure adjustment component to provide pressures of different ones of the sleep pressure profiles as the sleeper changes sleep position. In some embodiments the process commands the pressure adjustment component to provide pressures of different ones of the sleep pressure profiles as the sleeper changes sleep stage. In some embodiments the process commands the pressure adjustment component to provide pressures of different ones of the sleep pressure profiles as the sleeper changes sleep position or the sleeper changes sleep stage. In some embodiments the process commands the pressure adjustment component to change pressures at different rates depending on the sleep stage of the sleeper. In some embodiments the process commands the pressure adjustment component to provide pressures of a pressure profile(s) that varies over time in response to receiving an indication from biometric sensors that the sleepers, or at least one of them in some embodiments, is asleep. In some embodiments, the controller monitors sleep performance or disruptions and/or movement using information from the biometric sensors and may enable or disable this pressure profile based on the monitoring outcome(s). In some embodiments, the controller monitors sleep performance or disruptions and/or movement using information from the biometric sensors and may modulate or change this pressure profile characteristics, such as rate of change of the pressures, magnitude of pressure changes and modulating patterns, or location of zones where pressure is modulated, based on the monitoring outcome(s). In some embodiments, the controller monitors body specific pressure points using information from the pressure sensors and may modulate or change this pressure profile characteristics, such as location of zone(s) where pressure is modulated, rate of change of the pressures, or magnitude of pressure changes and modulating patterns, based on the monitoring outcome(s).

In some embodiments the controller may vary commands to the pressure adjustment component to provide different pressures than indicated by a particular sleep pressure profile, for example to provide a different sleep pressure profile. The controller may do so from time-to-time, generally on different days, in order to determine if the sleeper sleeps better with the different sleep pressure profile. In some embodiments the process may determine if the user has slept better using information from biometric sensors. In some embodiments the process determines if the sleeper slept better based on a metric of sleep. In some embodiments the metric of sleep is a total time of sleep in a night. In some embodiments the metric is a total time of sleep in a sleep deeper than a predetermined sleep stage. In some embodiments the metric is a total time of sleep minus an amount of time the user has been aroused during the night's sleep. In some embodiments the process may utilize the different sleep profile multiple times across multiple nights, and use an average, or some other statistically calculated value, for determining whether the sleeper slept better with the different sleep pressure profile than with the sleeper's then current particular sleep pressure profile. In response to the controller determining that the sleeper slept better with use of the different sleep pressure profile, the controller may set the different sleep pressure profile as the particular sleep pressure profile for the sleeper.

In block 415 the process commands the pressure adjustment component to perform wake-up operations. In some embodiments the process commands the pressure adjustment component to perform wake-up operations at a time based on a target wake up time for the sleeper. In some embodiments the target wake-up time is a time selected by the sleeper. In some embodiments the target wake-up time is determined by the controller based on information of a calendar for the sleeper, for example as provided by a smartphone or other compute device of the sleeper. In some embodiments the target wake-up time is based on a circadian rhythm of the sleeper determined by the controller, for example using information from biometric sensors.

In some embodiments the wake-up operations include the pressure adjustment component providing time-varying pressures across the sleep surface. In some embodiments the time-varying pressures form one or more patterns of pressures that vary over time. In some embodiments the one or more patterns of pressure are selectable by a sleeper. In some embodiments the one or more patterns may increase in amplitude and/or frequency as the target wake-up time approaches, and/or after the target wake-up time has been reached, if the sleeper has not yet awaken. In some embodiments one sleep pressure profile may be used for pre-target wake-up time wake-up operations, and another different sleep pressure profile may be used for post-target wake-up time operations if the sleeper is still asleep. In some embodiments the process also provides audio correlated to the time-varying pressures. In some embodiments the correlation is a synchronization of timing of audio sounds with timing of variations in pressure.

In block 417 the process commands the pressure adjustment component to perform arise operations. In some embodiments the process commands the pressure adjustment component to perform arise operations upon determining that the sleeper is awake. In some embodiments the process determines the sleeper is awake based on information from sensors. In some embodiments the sensors are biometric sensors. In some embodiments the arise operations include the pressure adjustment component providing increased firmness to the sleep surface. In some embodiments the arise operations include the pressure adjustment component providing increased pressure.

The process thereafter returns.

Figure 5:
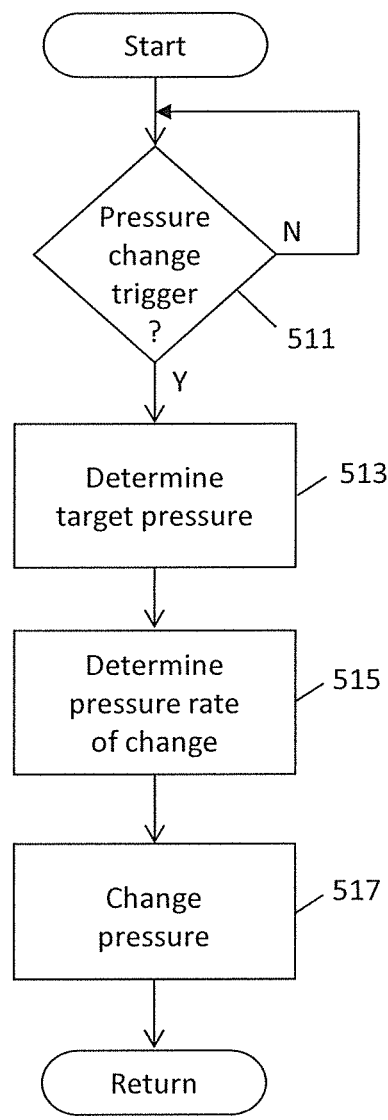
FIG. 5 is a flow diagram of a process for adjusting firmness of a sleep surface of a bed in accordance with aspects of the invention.

FIG. 5 is a flow diagram of a process for adjusting firmness of a sleep surface of a bed in accordance with aspects of the invention. In some embodiments the process is performed by a bed with a pressure adjustment component. In some embodiments the process is performed by a controller of a bed with a pressure adjustment component. In some embodiments the process is performed by a controller, which may be a processor, and in other embodiments, this computation is performed on a remote server coupled to the controller over a network. In some embodiments the processor receives information indicative of pressure on a sleep surface of a bed. In some embodiments the processor receives information from pressure sensors indicating pressure on at least a portion of the sleep surface, and in some embodiments the processor receives information from biometric sensors of the bed, or associated with a user of the bed. In some embodiments the process of FIG. 5 implements operations of block 415 of the process of FIG. 4.

In block 511 the process determines if a pressure profile change event has occurred. In some embodiments the process determines that the pressure profile change event has occurred upon a sleeper in the bed changing a sleep position. In some embodiments the sleeper has a plurality of predefined sleep positions. In some embodiments the predefined sleep positions include some or all of sleeping on the sleeper's left side, sleeping on the sleeper's right side, sleeping on the sleeper's back, and sleeping on the sleeper's front. In some embodiments the predefined sleep positions may include other sleep positions. In some embodiments the process in addition or instead determines that the pressure profile change event has occurred upon a sleeper in the bed changing a sleep stage. In some embodiments the sleep stages include a light sleep stage, a deep sleep stage, and a REM sleep stage. In some embodiments the sleep stages include N1, N2, N3, N4, and REM sleep stages. In some embodiments the sleep stages include N1, N2, slow wave sleep and REM sleep stages.

If a pressure profile change event has not occurred, the process continues to perform operations of block 511. If a pressure profile change event has occurred, the process continues to block 513.

In block 513 the process determines target pressures for pressure adjustment devices of the pressure adjustment component. In some embodiments the pressure adjustment devices include bladders for holding fluids (in gaseous state in some embodiments, in liquid state in some embodiments). In some embodiments the process determines target pressures based on a selected sleep pressure profile for the sleeper.

In some embodiments the selected sleep pressure profile utilized by the process is selected from one of a plurality of sleep pressure profiles for the sleeper. In some embodiments selection of the sleep pressure profile is based on sleeper position and/or sleep stage of the sleeper. For example, FIG. 6 is a table of pressure settings for use in controlling firmness of a sleep surface based on sleeper position and sleep stage, in accordance with aspects of the invention. The table of FIG. 6, or information of the table, may be used in some embodiments in implementing operations of the process of FIG. 5, or by the controller of FIG. 1, or in other processes discussed herein.

FIG. 6 indicates, in a left-most column, four particular sleep positions for a sleeper. For the purposes of example, the positions include on the sleeper's side, on the sleeper's side with the sleeper in the fetal position, on the sleeper's back, and on the sleeper's front. In various embodiments not all of the positions may be present in the table, and in various embodiments other or additional positions may be present in the table.

FIG. 6, in an upper-most row, sleep stages for the sleeper. In the table of FIG. 6, the sleep stages include N1, N2, N3, N4, and REM sleep stages. In some embodiments some of the sleep stages may be consolidated. In some embodiments other variations of sleep stages may be used.

The sleep positions and sleep stages provide an index for selection of a sleep pressure profile. In FIG. 6, sixteen possible sleep pressure profiles are available for selection. For example, for a side position for the sleeper, sleep pressure profiles $S_1$, $S_2$, $S_3$, $S_4$, $S_5$ are selected if the sleep stage of the sleeper is N1, N2, N3, N4, REM, respectively, and so on for each of the listed sleep positions and sleep stages. Each of the sleep pressure profiles specify target pressure(s) for pressure devices under a sleep surface. In some embodiments the target pressure(s) are specified for pressure devices based on zone, with for example one or more (and generally a plurality) of pressure devices for each zone of the sleep surface. In some embodiments the target pressure(s) are specified for individual pressure adjustment devices. In various embodiments some of the sleep pressure profiles may be the same, and some of the sleep pressure profiles may specify the same target pressure for some of the pressure adjustment devices. Moreover, as discussed herein, in various embodiments the sleep pressure profiles may change over time, for example due to testing of other sleep pressure profiles, which, if they improve sleep of the sleeper over a sleep pressure profile, replace that sleep pressure profile.

Returning to FIG. 5, in block 515 the process determines a rate of change for adjusting pressure of the pressure adjustment devices. In some embodiments the rate of change is determined implicitly, for example as a total time to be taken in adjusting the pressure. In some embodiments the rate of change is determined explicitly, for example as a rate at which pressure is to be adjusted, which may be in some embodiments as a percentage change in pressure and which may be in some embodiments as an absolute change in pressure. In some embodiments the rate of change is determined based on a sleep stage of the sleeper. In some such embodiments the rate of change may be determined to be faster for some sleep stages and slower for other sleep stages. In some embodiments the rate of change is determined to be faster for deeper sleep stages and slower for lighter sleep stages. In some embodiments a faster rate of change changes the pressure of the pressure device to the target pressure in six seconds or less, and in some embodiments in fifteen seconds or less. In some embodiments a slower rate of change changes the pressure of the pressure device to the target pressure in over one minute, and in some embodiments in between one and three minutes. In some embodiments the rate of change is a rate expected to not awake the sleeper, with the sleeper being easier to wake in lighter sleep stages than deeper sleep stages. In some embodiments N1 is a lighter sleep stage than N4. In some embodiments N1 and N2 are considered light sleep stages, and N3 and N4 are considered deeper sleep stages.

In block 517 the process commands the pressure(s) of the pressure devices to be changed to the new target pressure(s) determined in block 513, and at the rate of change determined in block 515.

The process thereafter returns.

Figure 7:
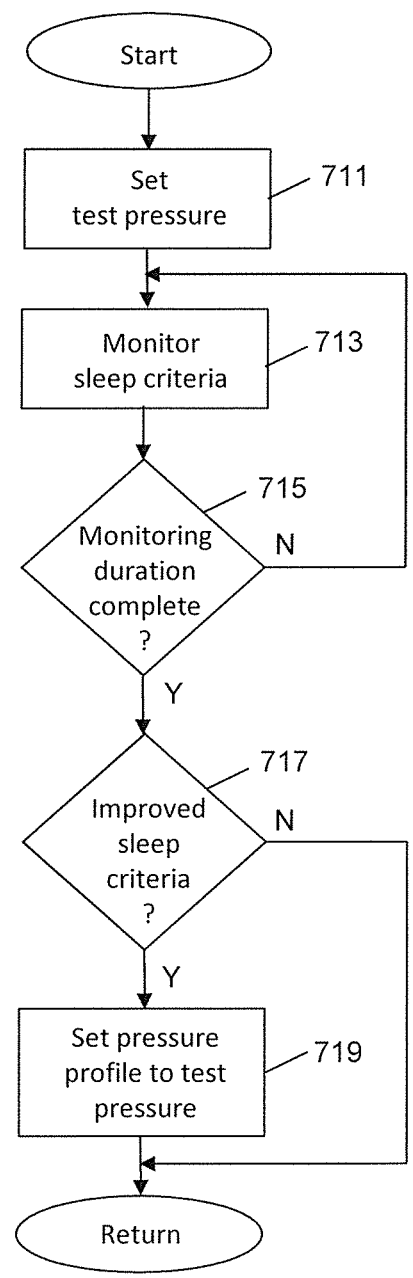
FIG. 7 is a flow diagram of a process for use in iteratively adjusting parameters for use in controlling firmness of a sleep surface of a bed in accordance with aspects of the invention.

FIG. 7 is a flow diagram of a process for use in iteratively adjusting parameters for use in controlling firmness of a sleep surface of a bed in accordance with aspects of the invention. In some embodiments the process is performed by a bed with a pressure adjustment component. In some embodiments the process is performed by a controller of a bed with a pressure adjustment component. In some embodiments the process is performed by a controller, which may be a processor, and in other embodiments, this computation is performed on a remote server coupled to the controller over a network. In some embodiments the processor receives information indicative of pressure on a sleep surface of a bed. In some embodiments the processor receives information from pressure sensors indicating pressure on at least a portion of the sleep surface, and in some embodiments the processor receives information from biometric sensors of the bed, or associated with a user of the bed.

In block 711 the process commands pressure of pressure devices using pressures of a test pressure profile for the sleep surface of the bed. In some embodiments the process uses the test pressure profile in place of one of the pressure profiles discussed herein. For example the test pressure profile may be used in place of the pre-sleep pressure profile, or one of the sleep pressure profiles (for example, using the nomenclature of the table of FIG. 6, the pressure profile $S_3$, or the pressure profile $f_4$, or one of the other sleep pressure profiles), or the wake-up pressure profile, or the arise pressure profile.

In block 713 the process measures one or more sleep criterion or metric. For example the process may monitor a time taken to fall asleep once a sleeper enters the bed. Also for example, the process may monitor a time a total time a sleeper has slept during the night. Also for example, the process may monitor a total time of deep wave sleep the sleeper had during the night. In addition, other sleep related criteria or metrics may be used. In some embodiments the process measures the sleep criteria or metrics based on information from sensors. In some embodiments the process measures the sleep criteria or metrics based on information from biometric sensors.

In block 715 the process determines if the monitoring duration time is complete. In some embodiments the monitoring duration encompasses an entire night's sleep. In some embodiments the monitoring duration encompasses a part of a night's sleep. In some embodiments the monitoring duration is complete once the sleeper falls asleep. If the monitoring duration is complete the process continues to block 717, otherwise the process continues measuring sleep criteria in block 713.

In block 717 the process determines if the measured criteria or metrics indicates an improvement in sleep for the sleeper compared to previously measured criteria or metrics for the sleeper using the pressure profile that would otherwise have been used. In some embodiments an improvement in sleep performance is falling asleep faster. In some embodiments an improvement in sleep performance is a longer duration asleep during the night. In some embodiments an improvement in sleep performance is reduced interruption to sleep during the night. In some embodiments the process may repeat the operations of block 711-715 multiple times, for example over multiple nights, and use an average, or some other statistically calculated value, for determining whether the sleeper experienced an improvement in sleep with the test pressure profile rather the pressure profile that would have been otherwise used.

If an improvement in sleep performance occurred, the process continues to block 719. Otherwise the process returns.

In block 719 the process replaces the pressure profile that would have been otherwise used with the test pressure profile.

The process thereafter returns.

Although the invention has been discussed with respect to various embodiments, it should be recognized that the invention comprises the novel and non-obvious claims supported by this disclosure.

What is claimed is:

1. A bed including a sleep surface having controllable firmness, comprising:
   pressure devices used in adjusting firmness of the sleep surface;
   pressure sensors configured to sense indications of pressure of the sleep surface; and
   a controller configured to command the pressure devices to achieve target pressures based on a sleep position of a sleeper on the sleep surface and a sleep stage of the sleeper on the sleep surface, as indicated by a plurality of target pressure profiles specifying the target pressures, the plurality of target pressure profiles including target pressure profiles that differ for each of a plurality of sleep positions and a plurality of sleep stages;
   with the controller further configured to, from time-to-time:
      command the pressure devices to achieve a set of test pressures different than the target pressures specified by the target pressure profiles;
      determine if a total sleep time for the sleeper on the sleep surface indicates increased total sleep time using the test pressures different than the target pressures specified by the target pressure profiles; and, in response to determining that the total sleep time for the sleeper indicates increased total sleep time, replace the target pressures specified by the target pressure profiles with the test pressures.

2. The bed of claim 1, wherein the the target pressures are target pressures of a pre-sleep profile associated with the sleeper.

3. The bed of claim 2, wherein the controller is configured to begin commanding the pressure devices to achieve the target pressures, or the test pressures, in response to receiving an indication that the sleeper is on the sleep surface.

4. The bed of claim 3, wherein the pre-sleep profile specifies the target pressures that vary over time in a repetitive pattern.

5. The bed of claim 1, further comprising biometric sensors configured to provide biometric information regarding the sleeper.

6. The bed of claim 5, wherein the controller is further configured to determine the sleep stages of the sleeper based on the biometric information regarding the sleeper.

7. The bed of claim 6, wherein the controller is configured to command the pressure devices to achieve the target pressures specified by a sleep target pressure profile in response to receiving an indication from the biometric sensors that the sleeper is asleep.

8. The bed of claim 1, wherein the controller is configured to utilize the test pressures over multiple nights, and to use a statistically calculated value for total sleep time.

* * * * *